United States Patent
Bhushan et al.

(10) Patent No.: US 6,296,871 B1
(45) Date of Patent: Oct. 2, 2001

(54) STABLE SOLID PHARMACEUTICAL COMPOSITIONS CONTAINING ENALAPRIL MALEATE

(75) Inventors: Indu Bhushan, New Delhi; Jitendra Krishan Somani, Haryana, both of (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/304,413

(22) Filed: May 3, 1999

(30) Foreign Application Priority Data

Apr. 12, 1998 (IN) .......................................... 3661/98

(51) Int. Cl.⁷ ................................. A61K 9/48; A61K 9/20

(52) U.S. Cl. .......................... 424/451; 424/452; 424/464; 424/465

(58) Field of Search ..................................... 424/451, 452, 424/464, 465; 435/188

(56) References Cited

U.S. PATENT DOCUMENTS

| 4,374,829 | | 2/1983 | Harris et al. . | |
| 4,537,887 | * | 8/1985 | Rooke et al. ......................... | 514/197 |
| 4,743,450 | | 5/1988 | Harris et al. . | |
| 4,793,998 | * | 12/1988 | Murthy et al. ........................ | 424/440 |
| 4,830,853 | * | 5/1989 | Murthy et al. ........................ | 424/440 |
| 5,562,921 | * | 10/1996 | Sherman .............................. | 424/465 |
| 5,690,962 | * | 11/1997 | Sherman .............................. | 424/489 |
| 5,891,474 | * | 4/1999 | Busetti et al. ........................ | 424/490 |

FOREIGN PATENT DOCUMENTS

WO 98/26765    6/1998   (WO) .

* cited by examiner

Primary Examiner—Thurman K. Page
Assistant Examiner—Isis Ghali
(74) Attorney, Agent, or Firm—Jayadeep R. Deshmukh, Esq.

(57) ABSTRACT

A stable solid pharmaceutical composition in the form of tablets or capsules is disclosed including enalapril maleate as active ingredient and pharmaceutically acceptable excipients wherein at least one excipient is maleic acid or other edible desiccants.

4 Claims, No Drawings

US 6,296,871 B1

STABLE SOLID PHARMACEUTICAL COMPOSITIONS CONTAINING ENALAPRIL MALEATE

FIELD OF THE INVENTION

The present invention relates to a process for the preparation of a stable solid pharmaceutical composition in the form of tablets or capsules comprising enalapril maleate as active ingredient.

BACKGROUND OF THE INVENTION

The quality of a pharmaceutical dosage form is defined and specified in terms of measurable as well as non-measurable pharmaceutical attributes such as content of active ingredient, percent of impurities, rate at which the active ingredient dissolves, appearance, etc. A stable dosage form is one which retains all its desirable physical and chemical attributes upto a time when the dosage form is consumed by the patient. When a dosage form meets the specifications, of purity and strength of active ingredient upto a time when the dosage form is consumed by the patient it is considered as chemically stable. Strength herein refers to the amount of active ingredient in the dosage form. Chemical instability results in a decrease in the percent of active ingredient and consequently the desired therapeutic efficacy may be compromised. Moreover, degradation of the active ingredient may result in the formation of degradation products that are undesirable, for example, acetic acid formed as a result of degradation of aspirin has an unacceptable odor; or in the formation of degradation products that could have undesirable toxicity. It is thus quite apparent that stability is an essential component in the design of pharmaceutical dosage forms and that all pharmaceutical dosage forms must be designed to be stable.

Enalapril maleate, an angiotensin converting enzyme inhibitor, known through U.S. Pat. No. 4,374,829, is useful in the treatment of essential and renovascular hypertension. It is highly susceptible to decomposition and undergoes autocyclization to form diketopiperazine. In addition enalapril maleate may form diacids via hydrolysis or may undergo oxidation resulting in discoloration when formulated into pharmaceutical dosage forms.

U.S. Pat. No. 5,562,921 discloses that enalapril maleate degrades at a faster rate in the presence of some diluents namely microcrystalline cellulose, dibasic calcium phosphate, and tribasic calcium phosphate; lubricants, namely magnesium stearate and calcium stearate, and disintegrants such as crosspovidone, and sodium starch glycolate. The disclosed composition was free or substantially free of microcrystalline cellulose, cellulose derivatives or cellulose polymers, calcium phosphate, disintegrants, and magnesium stearate. At least 50% by weight of the pharmaceutical excipients in the composition were pharmaceutically acceptable water soluble substances such that the composition could dissolve sufficiently rapidly and not require the use of disintegrants.

U.S. Pat. No. 4,743,450 assigned to Warner-Lambert Company discloses a stable pharmaceutical composition containing an Angiotensin Converting Enzyme (ACE) inhibitor susceptible to cyclization, hydrolysis and discoloration. The disclosed composition is said to contain an alkali or alkaline earth metal carbonate to minimize cyclization and discoloration and also suitable amount of a saccharide to inhibit hydrolysis of the active ingredient.

U.S. Pat. No. 4,830,853 assigned to Warner-Lambert Company discloses a pharmaceutical composition containing an ACE inhibitor stabilized for oxidation and discoloration using 0.5–15% w/w of ascorbic acid and/or sodium ascorbate by weight of the combination with the drug and at least one lubricant and/or excipient or mixtures thereof which do not interfere with the functions of stabilizers.

U.S. Pat. No. 4,793,998 assigned to Warner-Lambert Company discloses a pharmaceutical composition containing from about 1 to 70% by weight of an ACE inhibitor and about 1–90% by weight of the stabilizer which contains either ascorbic acid alone or at least 10% w/w of ascorbic acid in combination with organic acids such as fumaric, maleic and citric acid as a cyclization and/or hydrolysis inhibitors with at least one lubricant and/or excipient.

U.S. Pat. No. 5,690,962 assigned to Apotex Corporation discloses a stable formulation made by reacting enalapril maleate with a sodium compound. The composition obtained is said to contain the reaction products enalapril sodium and disodium maleate and was more stable than a similar composition containing enalapril maleate. However, a disadvantage of such processing is that the active ingredient does not retain its chemical identity as it is converted from enalapril maleate to enalapril sodium.

In light of the foregoing, a principal object of the present invention is to provide a process for the preparation of a stable oral pharmaceutical composition in the form of tablets or capsules comprising enalapril maleate as the active ingredient and pharmaceutical excipients wherein at least one excipient is maleic acid or an edible dessicant. Use of maleic acid or an edible desiccant as one of the pharmaceutical excipients significantly reduces the rate of degradation of enalapril maleate in the formulation.

The pharmaceutical composition prepared according to the process of the present invention provides excellent stability inspite of the presence of several destabilizing excipients and thus provides greater flexibility in the choice of excipients for the formulation of enalapril maleate tablets.

According to one aspect of the process of the present invention, the pharmaceutical composition contains maleic acid. Enalapril maleate is an ester of enalapril and maleic acid. Maleic acid, a dicarboxylic acid, is commonly used in food products and beverages. It is acceptable for use as a pharmaceutical excipient/aid and is useful as an acidifying agent, a lubricant, and taste enhancer. Maleic acid may be present in an amount from 0.1% to 5% preferably from 0.1% to 1% by weight of the total weight of the composition.

According to another aspect of the process of the present invention, the pharmaceutical composition in the form of tablets contains an edible desiccant within the tablet itself. Suitable desiccants that can be used in the present invention are those that are edible, and include, for example, edible grades of silica gel, crystalline sodium, potassium or calcium aluminosilicate, colloidal silica, anhydrous calcium sulphate and the like. The desiccant may be present in an amount from about 1% to 20%, preferably from about 2% to 15% by weight of the total weight of the composition.

According to the present invention, the pharmaceutical composition also contains conventional pharmaceutical excipients that are well known to those skilled in the art including diluents, binders, disintegrants, lubricants, coloring agents, and others. Pharmaceutical excipients that may be used in the present invention may include diluents such as microcrystalline cellulose, lubricants such as magnesium stearate, and disintegrants such as cross-linked carboxy methyl cellulose sodium, which have been reported to be incompatible with enalapril maleate in prior art references.

DETAILED DESCRIPTION OF THE INVENTION

Example 1

This example illustrates the process for the preparation of a composition containing an edible desiccant. Tablets were prepared according to the composition given in Table 1.

TABLE 1

| Ingredient | Formulation 1 mg/Tablet | % w/w | Formulation 2 mg/Tablet | % w/w |
|---|---|---|---|---|
| Enalapril maleate | 5.03 | 2.19 | 5.03 | 2.19 |
| Edible Silica (SiO2) | 10.00 | 4.35 | — | — |
| Spray-dried lactose monohydrate | 80.00 | 34.78 | 80.00 | 34.78 |
| Microcrystalline Cellulose (MCC) | 127.97 | 55.64 | 139.97 | 60.86 |
| Cross-linked carboxymethylcellulose sodium | 3.00 | 1.30 | 3.00 | 1.30 |
| Glyceryl behenate | 4.00 | 1.74 | 2.00 | 1.74 |
| Total | 230.00 | 100.00 | 230.00 | 100.00 |

Cross-linked carboxymethyl cellulose was dried for 1 hr at 70° C. mixed with lactose monohydrate and microcrystalline cellulose and sieved through British Standard Sieve (BSS) No. 30. Enalapril maleate and SiO2 were passed through a BSS No.60 sieve, and the sieved materials were mixed together. Glyceryl behenate was passed through a BSS No. 60 sieve and blended with the mixture. The powder mixture was then compressed into tablets of average weight 230 mg.

The tablets were packed in high density polyethylene bottles with child resistant closure caps and stored at 60° C. for 15 days. A stability indicating assay procedure was used to determine the drug content and the total related substances (Total RS). The total RS values reduced from 6.33% (formulation 2) to 1.93% (formulation 1) when the desiccant was added to the formulation. The results indicate that the addition of an edible desiccant resulted in an improved stability of the composition. As per the pharmacopeal limits for enalapril maleate tablets, the total RS should not be more than 5%.

Example 2

This example illustrates the process for the preparation of a stable pharmaceutical composition containing maleic acid. Tablets were prepared according to the composition given in Table 2.

TABLE 2

| Ingredient | Formulation 3 mg/Tablet | % w/w | Formulation 4 mg/Tablet | % w/w |
|---|---|---|---|---|
| Enalapril maleate | 5.03 | 2.19 | 5.03 | 2.19 |
| Maleic acid | 1.00 | 0.435 | — | — |
| Spray-dried lactose monohydrate | 80.00 | 34.78 | 80.00 | 34.78 |
| Microcrystalline Cellulose (Emcocel XLM 90) | 138.97 | 60.42 | 139.97 | 60.86 |
| Cross-linked carboxymethyl cellulose sodium | 3.00 | 1.30 | 3.00 | 1.30 |
| Magnesium stearate | 2.00 | 0.87 | 2.00 | 0.87 |
| Total | 230.00 | 100.00 | 230.00 | 100.00 |

Cross-linked carboxymethyl cellulose sodium was dried for 1 hr at 70° C. Lactose monohydrate and microcrystalline cellulose were mixed with it and sieved through British Standard Sieve (BSS) No. 30. Enalapril maleate and maleic acid were passed through a BSS No.60 sieve, and the sieved materials were mixed together. The lubricant (magnesium stearate) was passed through a BSS No. 60 sieve and blended with the mixture. The powder mixture was then compressed into tablets of average weight 230 mg.

The tablets were packed as described in example 1. The total RS of tablets stored at 60° C. for 15 days was found to be 2.99% and 14.46% for formulation 3 and 4, respectively. The results indicate that the addition of maleic acid stabilizes the formulation even in the presence of magnesium stearate which is incompatible with enalapril maleate.

Example 3

This example illustrates the process for the preparation of a stable pharmaceutical composition containing maleic acid. Tablets were prepared according to the composition given in Table 3.

TABLE 3

| Ingredient | Formulation 5 mg/Tablet | % w/w | Formulation 6 mg/Tablet | % w/w |
|---|---|---|---|---|
| Enalapril maleate | 5.03 | 2.19 | 5.03 | 2.19 |
| Maleic acid | 1.00 | 0.435 | — | — |
| Spray-dried lactose monohydrate | 80.00 | 34.78 | 80.00 | 34.78 |
| Microcrystalline Cellulose | 138.97 | 60.42 | 139.97 | 60.86 |
| Cross-linked carboxymethylcellulose sodium | 3.00 | 1.30 | 3.00 | 1.30 |
| Zinc Stearate | 2.00 | 0.87 | 2.00 | 0.87 |
| Total | 230.00 | 100.00 | 230.00 | 100.00 |

The tablets were prepared and packed as described in example 1. The total RS of tablets stored at 60° C. for 15 days was found to be 2.07% and 7.59% for formulation 5 and 6, respectively. Maleic acid in combination with a compatible lubricant, zinc stearate, results in a further improvement in the stability of the formulation.

Example 4

This example illustrates the process for the preparation of a stable pharmaceutical composition containing maleic acid. Tablets were prepared according to the composition given in Table 4.

TABLE 4

| Ingredient | Formulation 7 mg/Tablet | % w/w | Formulation 8 mg/Tablet | % w/w |
|---|---|---|---|---|
| Enalapril maleate | 5.03 | 2.19 | 5.03 | 2.19 |
| Maleic acid | 1.00 | 0.435 | — | — |
| Spray-dried lactose monohydrate | 80.00 | 34.78 | 80.00 | 34.78 |
| Microcrystalline Cellulose | 136.97 | 60.42 | 139.97 | 60.42 |
| Cross-linked carboxymethylcellulose sodium | 3.00 | 1.30 | 3.00 | 1.30 |
| Glyceryl behenate | 4.00 | 0.87 | 2.00 | 0.87 |
| Total | 230.00 | 100.00 | 230.00 | 100.00 |

The tablets were prepared and packed as described in example 1. The total RS of the tablets at 60° C. for 15 days was found to be 0.62% and 6.33% for formulation 7 and 8, respectively. The results indicate that the addition of maleic acid in combination with glyceryl behenate as lubricant results in an improvement in the stability of formulation.

The tablets of formulation Nos. 1,3, 5 and 7 which showed enhanced stability at 60° C. for 15 days were subjected to stability studies for two months at 40° C. and 75% Relative Humidity. The total RS was found to be 1.90%, 2.78%, 0.131% and 0.83%, respectively, further confirming that enalapril maleate tablets were stabilized against degradation in the presence of an edible dessicant or maleic acid.

We claim:

1. A stable oral pharmaceutical composition in the form of tablets or capsules comprising:

(a) enalapril maleate as an active ingredient;
    (b) a stabilizer consisting essentially of an edible silica desiccant in an amount ranging from 1 to 20% by weight of the total weight of the composition; and
    (c) microcrystalline cellulose as an excipient.

2. The composition of claim 1 wherein the edible desiccant is present in an amount up to 10% by weight of the total weight of the composition.

3. The composition of claim 1 wherein the pharmaceutical composition contains a lubricant selected from the group consisting of zinc stearate and glyceryl behenate.

4. The composition of claim 1 wherein the pharmaceutical composition contains glyceryl behenate as an excipient.

* * * * *